US008478444B2

(12) United States Patent
Fuxman et al.

(10) Patent No.: US 8,478,444 B2
(45) Date of Patent: Jul. 2, 2013

(54) APPARATUS AND METHOD FOR CONTROLLING AUTOTROPH CULTIVATION

(75) Inventors: Adrian M. Fuxman, North Vancouver (CA); Sebastien Tixier, North Vancouver (CA); Gregory E. Stewart, North Vancouver (CA); Frank M. Haran, North Vancouver (CA); Johan U. Backstrom, North Vancouver (CA); Kelsey Gerbrandt, Burnaby (CA)

(73) Assignee: Honeywell ASCa Inc., Mississauga, Ontario (CA)

( * ) Notice: Subject to any disclaimer, the term of this patent is extended or adjusted under 35 U.S.C. 154(b) by 34 days.

(21) Appl. No.: 12/985,061

(22) Filed: Jan. 5, 2011

(65) Prior Publication Data

US 2012/0173023 A1    Jul. 5, 2012

(51) Int. Cl.
*G01N 15/06*   (2006.01)
*G01N 33/00*   (2006.01)
*G01N 33/48*   (2006.01)

(52) U.S. Cl.
USPC .............. 700/266; 422/50; 422/68.1; 422/62; 422/67

(58) Field of Classification Search
USPC ........................ 422/50, 68.1, 62, 67; 700/266
See application file for complete search history.

(56) References Cited

U.S. PATENT DOCUMENTS

| | | | |
|---|---|---|---|
| 5,132,094 A | 7/1992 | Godec et al. | |
| 5,408,838 A | 4/1995 | Yaeger et al. | |
| 5,984,002 A | 11/1999 | Kido et al. | |
| 6,792,331 B1 | 9/2004 | Hamstrom et al. | |
| 7,263,246 B1 | 8/2007 | Duan et al. | |
| 7,330,262 B2 | 2/2008 | Siepmann et al. | |
| 2005/0247574 A1 | 11/2005 | Varney | |
| 2005/0267639 A1 | 12/2005 | Sharma et al. | |
| 2008/0311836 A1 | 12/2008 | Bhattacharya | |
| 2009/0126265 A1 | 5/2009 | Rasmussen et al. | |
| 2011/0136212 A1 | 6/2011 | Parsheh et al. | |

OTHER PUBLICATIONS

"GMP343 Carbon Dioxide Probe for Demanding Measurements", Vaisala, 2009, 2 pages.
"Vaisala CARBOCAP Carbon Dioxide Probe GMP343", User's Guide, Vaisala, 2007, 96 pages.
"InPro 5000 CO2 Sensors, Instruction manual", Mettler Toledo, Sep. 2006, 19 pages.
"GM70 Hand-Held Carbon Dioxide Meter for Spot-Checking Applications", Vaisala, 2009, 2 pages.
"GMD/W20 Series Carbon Dioxide Transmitters for Demand Controlled Ventilation Applications", Vaisala, 2009, p. 96-97.
"GMM111 Carbon Dioxide Module", Vaisala, 2009, 2 pages.
"GMM2OW CO2 module", Vaisala, Nov. 16, 1999, 5 pages.

(Continued)

*Primary Examiner* — Brian J Sines (57) ABSTRACT

A method includes receiving at least one measurement of a dissolved carbon dioxide concentration of a mixture of fluid containing an autotrophic organism. The method also includes determining an adjustment to one or more manipulated variables using the at least one measurement. The method further includes generating one or more signals to modify the one or more manipulated variables based on the determined adjustment. The one or more manipulated variables could include a carbon dioxide flow rate, an air flow rate, a water temperature, and an agitation level for the mixture. At least one model relates the dissolved carbon dioxide concentration to one or more manipulated variables, and the adjustment could be determined by using the at least one model to drive the dissolved carbon dioxide concentration to at least one target that optimize a goal function. The goal function could be to optimize biomass growth rate, nutrient removal and/or lipid production.

23 Claims, 4 Drawing Sheets

OTHER PUBLICATIONS

"GMM220 Carbon Dioxide Modules for Demanding OEM Applications", Vaisala, 2010, 2 pages.
"GMT220 Series Carbon Dioxide Transmitters for Industrial Applications", Vaisala, 2009, 2 pages.
"GMW115 Carbon Dioxide Transmitter for Demand-controlled Ventilation", Vaisala, 2009, 2 pages.
"SenseAir, Product Specification, CO2 Engine K22-OC", May 4, 2007, 8 pages.
"Transmitter CO2 5100 e, Sensor InPro 5000, CO2 measuring systems for fermentation control, Technical data", Mettler Toledo, 12 pages, Sep. 2006.
Lichtenfeld, Rachel "Paint Booth Project Conserves Energy, Reduces Costs", College of Engineering, Nov. 2, 2007, vol. 79, The Ohio State University, pp. 1-2, http://engineering.osu.edu/nie/article.
"Honda Environmental Annual Report 2008, Operational Domains, FY2008 Regional Initiatives", Honda Motor Co., Ltd. 2009, http:i/world.honda.com/environment/ecology/200Breport/overseas/overseas11/, 4 pages. (Printed at least as early as Apr. 22, 2009).
Paul S. Fountain, "Apparatus and Method for Optimizing a Liquefied Natural Gas Facility", U.S. Appl. No. 11/708,957, filed Feb. 21, 2007.
Howard M. Boder, "Apparatus and Method for Optimizing Operation of Sugar Dryers", U.S. Appl. No. 12/029,587, filed Feb. 12, 2008.
H. Van Dyke Parunak, "Practical and Industrial Applications of Agent-Based Systems", 1998, 41 pages, see esp. p. 18.
"Direct-Fired Healing & Ventilating", The AA Series, AbsolutAire, Dec. 2004, 16 pages, see esp. p. 12-13.
Howard M. Boder, et al. "Apparatus and Method for Controlling an Air Supply for Drying Painted Vehicles and Other Objects", U.S. Appl. No. 12/033,134, filed Feb. 19, 2008.
Adam Krolak, et al. "In-Situ Sensor for Automated Measurements of Gas Content in Liquid and Related System and Method", U.S. Appl. No. 121899,707, filed Oct. 7, 2010.
Alabi, Abayomi O., et al."Microalgae Technologies & Processes for Biofuels/ Bioenergy Production in British Columbia: Current Technology, Suitability & Barriers to Implementation", British Columbia innovation Council, Jan. 14, 2009, 88 pages, Seed Science Ltd.
Ferrell, John, et al. "National Algal Blofuels Technology Roadmap", Energy Efficiency & Renewable Energy, Biomass Program, May 2010, 140 pages, U.S. Department of Energy, College Park, Maryland.
"Fluorometer and Scattering Meter", WET Labs ECO FLNTU•, WET Labs, Inc., www.wetlabs.com, Sep. 21, 2010, 1 page.
Notification of Transmittal of the International Search Report and the Written Opinion of the International Searching Authority, or the Declaration dated Apr. 10, 2012 in connection with International Patent Application No. PCT/CA2012/000005.
Robert O'Leary, et al., "Attenuated Total Reflection Spectroscopy method for measuring dissolved CO2 concentration in Beer", VitalSensors Technologies, LLC, 4 pages, Jan. 2006.
"OxyGuard CO2 Portable, Portable Dissolved CO2 Analyser", OxyGuard, 2 pages, May 2008.
"SenseAir, Product Description, CO2 Engine K30, Sensor module and OEM platform", 12 pages, May 2007.
"SenseAir, Product Description, CO2 Engine-BLG/ELG, Sensor module for environment parameters logging", 13 pages, Feb. 2010.
"Life Sciences products", YSI, 21 pages, at least as early as Jul. 2010.
"Pipette calibration specials", www.johnmorris.com.au, 4 pages, at least as early as Aug. 2007.

APPARATUS AND METHOD FOR CONTROLLING AUTOTROPH CULTIVATION

GOVERNMENT LICENSE RIGHTS

This invention was made with government support under contract DEFC2610FE0002568 from the United States Department of Energy. The government has certain rights in the invention

TECHNICAL FIELD

This disclosure relates generally to control systems. More specifically, this disclosure relates to an apparatus and method for controlling autotroph cultivation.

BACKGROUND

Wastewater can include a variety of undesirable components. Accordingly, wastewater is often treated in large wastewater treatment plants. One wastewater treatment process involves the use of algae to convert undesirable wastewater components into more desirable components. However, difficulties can arise in creating the right environment for the algae to thrive and thereby provide optimal performance.

SUMMARY

This disclosure provides an apparatus and method for controlling autotroph cultivation.

In a first embodiment, an apparatus includes a controller configured to determine how to adjust one or more manipulated variables to control one or more controlled variables. The one or more manipulated variables and the one or more controlled variables are associated with a mixture of fluid containing an autotrophic organism. The one or more controlled variables include a dissolved carbon dioxide concentration of the mixture. The one or more manipulated variables include a carbon dioxide flow rate for the mixture.

In a second embodiment, a method includes receiving at least one measurement of a dissolved carbon dioxide concentration of a mixture of fluid containing an autotrophic organism. The method also includes determining an adjustment to one or more manipulated variables using the at least one measurement. The method further includes generating one or more signals to modify the one or more manipulated variables based on the determined adjustment.

In a third embodiment, a computer readable medium embodies a computer program. The computer program includes computer readable program code for receiving at least one measurement of a dissolved carbon dioxide concentration of a mixture of fluid containing an autotrophic organism. The computer program also includes computer readable program code for determining an adjustment to one or more manipulated variables using the at least one measurement. The computer program further includes computer readable program code for generating one or more control signals to modify the one or more manipulated variables based on the determined adjustment.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 4, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device(s) or system(s).

Figure 1:
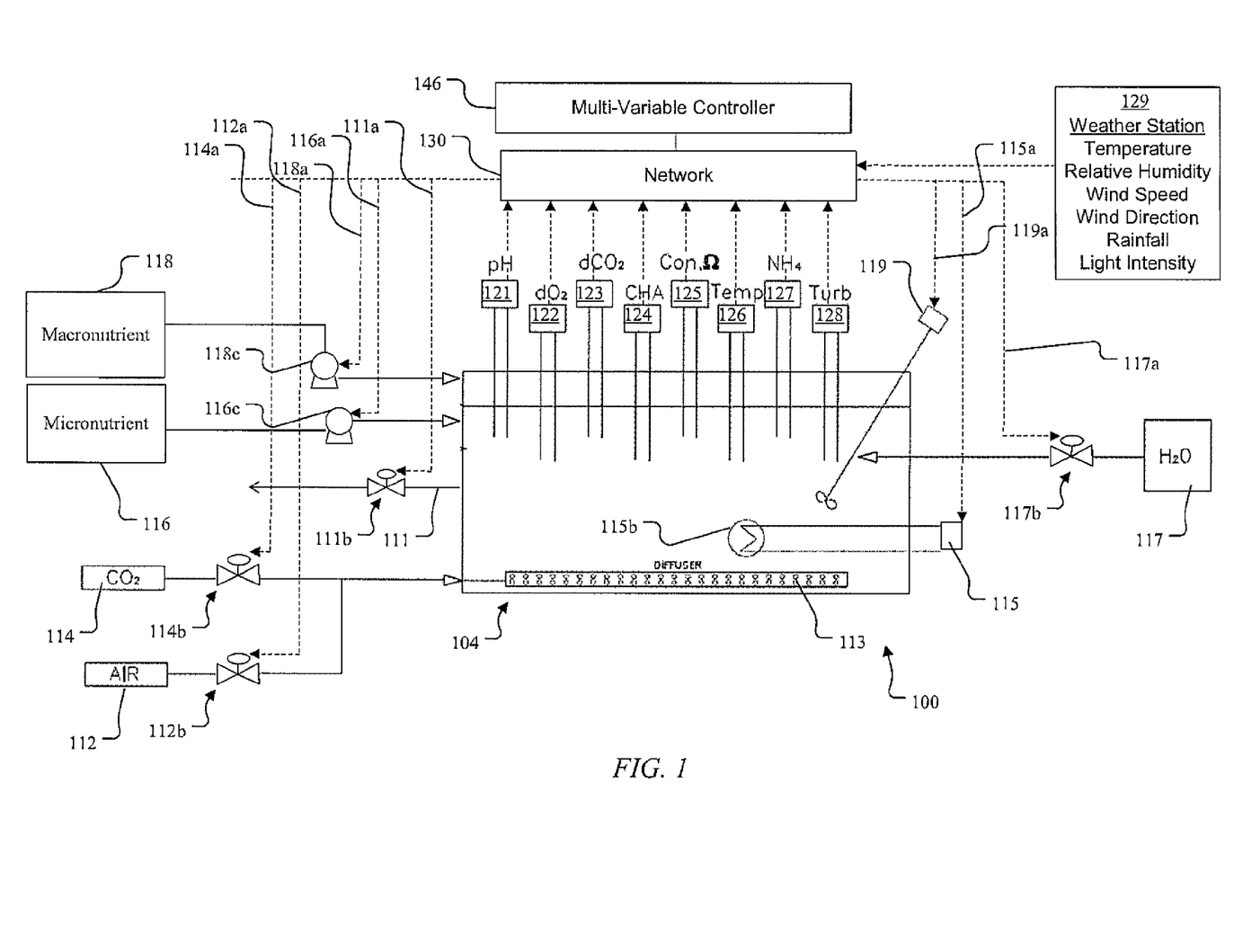
FIG. 1 illustrates an example system for controlling a mixture of fluid and an autotrophic organism according to this disclosure.

FIG. 1 illustrates an example system 100 for controlling a mixture of fluid and an autotrophic organism according to this disclosure. The embodiment of the system 100 shown in FIG. 1 is for illustration only. Other embodiments of the system 100 may be used without departing from the scope of this disclosure.

Algae cultivation is becoming more and more important in various processes, such as water/wastewater treatment processes. This is largely due to the ability of algae to consume and/or sequester carbon dioxide ($CO_2$) and various undesirable components such as nitrogen, which the algae may view as a nutrient. Additionally, algae is widely viewed as a promising biofuel.

In a conventional water treatment system, gaseous carbon dioxide and air are supplied to an algae tank with water in order to drive a pH value of the mixture towards a desired set point. The assumption in such a conventional configuration is that dissolved carbon dioxide and pH are so tightly related that a pH set point can be used as a control measure for carbon dioxide control. This disclosure, however, recognizes that this is not necessarily the case. As described in more detail below, the assumed carbon dioxide-pH relationship may not hold true in the presence of complicated chemical mixtures, such as those encountered in wastewater systems.

Recognizing the inaccuracy of the conventional assumptions, this disclosure discloses a control technique that includes measuring dissolved carbon dioxide levels ($dCO_2$) and possibly pH levels to determine how an algae system is functioning. Also, a multivariable or other controller could be used to maintain dissolved carbon dioxide and possibly pH levels near their optimal targets. In some embodiments, in order to maximize algae growth rate, carbon dioxide uptake rate, and nutrient uptake rate, an algae system may be maintained at or near its optimal conditions by making one or more adjustments to the algae system. Example adjustments could include adjustments to light exposure, water temperature, water chemical composition, harvest rate, agitation rate, air flow rate, pH, and level of dissolved carbon dioxide.

Note that the following description routinely describes the system 100 as being used for treating wastewater with algae cultivation. However, the system 100 or its associated control mechanisms could be used in various other environments. For example, the system 100 or its control mechanisms could be used for algae cultivation in general water (including fresh water or salt water) or other types of fluid. Also, wastewater being treated may come from a variety of sources, including municipal wastewater and industrial wastewater. Furthermore, organisms other than algae may be utilized to treat wastewater, water, or other fluids. Such organisms could include autotrophic organisms that receive their energy from light (such as photoautotrophs like microalgae, macroalgae, phytoplankton and cyanobacteria) or from chemicals (such as chemoautotrophs). Algae or other organisms could be combined with heterotrophic bacteria to treat wastewater. In particular embodiments, the growth of algae or other organisms may be the primary focus of the cultivation, such as in configurations in which the algae or other organisms are to be used as a biofuel. In such biofuel configurations, the algae may not be designed to treat a fluid. Additionally, although the use of a multivariable controller is described with respect to FIGS. 1-4, any other suitable controller can be used. Such controllers may include PID controllers, model predictive controllers, and the like.

As shown in FIG. 1, the system 100 includes components that supply certain items to an algae tank 104. In this example, the components include an air component 112 for supplying air, a carbon dioxide component 114 for supplying carbon dioxide, and a thermal energy component 115 for supplying thermal energy. The components also include a micronutrients component 116 for supplying micronutrients, a macronutrients component 118 for supplying macronutrients, and a water ($H_2O$) component 117 for supplying water. A mixing component 119 agitates the mixture within the algae tank 104. To supply respective items into the algae tank 104, any suitable equipment may be provided. Examples in FIG. 1 include valves 112b, 114b, 117b; pumps 116c, 118c; and an electric immersion heater 115b. Any other suitable equipment could be used with the various actuators in FIG. 1.

In addition to these components, one or more lines 111 may be provided for items to leave the tank 104. Example items leaving the tank 104 include water and algae, although other items may be removed from the tank 104. To facilitate such removal, a valve 111b may be utilized.

Commands may be communicated over a network 130 through paths 111a, 112a, 114a, 116a, and 118a to control the valves 111b, 112b, 114b and pumps 116c, 118c. These commands can be used to control the supply of air, carbon dioxide, and micro/macronutrients introduced to the tank 104 and to control the flow of material leaving the tank 104. The air and carbon dioxide may be supplied to the algae tank 104 via a diffuser 113.

Commands may also be sent through paths 115a, 117a, and 119a to control the mixture temperature using the electric immersion heater 115b, a speed or agitation level of a mixer of the mixing component 119, and an amount of water introduced into the tank (for leveling) using valve 117b. As described below, the commands sent over the network 130 may be provided by a multivariable controller 146. In other embodiments, the commands may be sent by any other suitable controller and/or controllers. Note that wired or wireless communication paths could be used in the system 100.

After being processed in the algae tank 104, processed fluid may be delivered through the outlet line 111 to any suitable location. Although a particular configuration is shown in FIG. 1, the system 100 may be modified in any number of ways. For example, while particular components are shown in this example embodiment, other or additional components may be used. As specific examples, light may be artificially introduced into the algae tank 104, or other chemicals may be supplied to the algae tank 104. Also, although only one algae tank 104 is shown in this example, multiple algae tanks 104 may be utilized. Further, in some embodiments, the algae tank 104 may interact with the ambient environment, while in other embodiments the algae tank 104 may be closed with certain parameters (such as light) introduced through a transparent cover or artificially introduced. Additionally, the algae tank 104 may be arranged in a continuous or batch process. The ambient environment could have its own variables, such as temperature, light intensity, and humidity.

Various factors can affect and alter the operation of the system 100. For example, light intensity or a temperature of the ambient environment may vary over time. Accordingly, certain components can be used in order to keep the algae tank 104 operating at or near optimal conditions. In this example, in order to measure the conditions of the algae tank 104, various sensors may be provided in the system 100. Example sensors may include a pH sensor 121, a dissolved oxygen sensor 122, a dissolved carbon dioxide sensor 123, a chlorophyll A (CHA) sensor 124, a conductivity ($\Omega$) sensor 125, a temperature sensor 126, a macronutrients sensor 127, and a turbidity sensor 128. Each sensor 121-128 measures its respective characteristic(s) and can communicate the measurements through the network 130 to the multivariable controller 146. Each sensor 121-128 may be of any suitable type for measuring its respective characteristic(s). In some embodiments, the dissolved carbon dioxide sensor 123 may be implemented as shown in U.S. patent application Ser. No. 12/899,707, which is hereby incorporated by reference. Additionally, in particular configurations, the sensors 121-128 may be spatially distributed and have any suitable arrangement.

In addition to measurements of the algae tank 104 itself, measurements may also be taken at a weather station 129. Among other things, the weather station 129 may measure parameters of the ambient environment, such as temperature, relative humidity, wind speed, rainfall, and light intensity. This measured weather information may be communicated to the multivariable controller 146 through the communication network 130.

To facilitate more accurate control over the system 100, the multivariable controller 146 can be used to make automatic process adjustments to control and optimize the operation of the system 100. In general, the system 100 is associated with "process variables," which represent various aspects of the system 100. The multivariable controller 146 may operate by attempting to maintain at least one "controlled variable" (CV) at or near a desired value or within a desired operating range. The multivariable controller 146 attempts to maintain the controlled variable(s) by altering one or more "manipulated variables" (MVs), such as by controlling an opening of one or more valves or otherwise controlling one or more actuators. A "disturbance variable" (DV) represents a process variable that affects a controlled variable, where the disturbance variable can be considered by the controller 146 but generally cannot be controlled by the controller 146 (such as ambient temperature or fluid composition). As examples of the above variables, dissolved carbon dioxide and pH levels may be controlled variables. Air flow rate, carbon dioxide flow rate, and heating may be manipulated variables. Light intensity, ambient temperature, and humidity may be disturbance variables. Other disturbance variables may include fluid composition, algae speciation, wind conditions, a presence of one or more predator, and a presence of bacteria. By controlling certain controlled variables, the multivariable controller 146 may optimize the process performed by the system 100.

In some embodiments, the multivariable controller 146 may use one or more mathematical models of the process being controlled. The models relate independent variables (manipulated and disturbance variables) to dependent variables (controlled variables). The models can be developed during the design of the multivariable controller 146, such as by using step-test data. The models can then be used to control the system 100 when the multivariable controller 146 goes on-line or is activated. For example, the controller 146 may use the models to predict the future values of the controlled variables and to calculate and implement adjustments to the manipulated variables to maintain the controlled variables within their defined limits. As particular examples, the multivariable controller 146 may use the models to keep the mixture in the algae tank 104 within acceptable dissolved carbon dioxide and pH ranges. In particular embodiments, a model may be updated based on measured changes to the controlled variables after adjustments to the manipulated variables.

The multivariable controller 146 could also operate at any suitable frequency in the system 100. For example, the multivariable controller 146 could operate at a 30-second interval. During each interval, the multivariable controller 146 can be used to make automatic process adjustments to control and optimize the system 100.

Note that the use of a multivariable controller that operates using one or more models is for illustration only. As noted above, any other suitable controller 146 could be used here. This can include controllers that do not operate using mathematical models or any other suitable control technique.

The use of the multivariable or other controller 146 can provide various benefits in the system 100 depending on the implementation. For example, the controller 146 can reduce the expense associated with operation of the system 100. As a particular example, absent the multivariable controller 146, different manipulated variables could be controlled independently, which can create oscillatory competition between modifications of the manipulated variables. By using a multivariable controller that considers how both manipulated variables interoperate, such oscillatory effects may be mitigated if not eliminated, which can reduce expenses. Better control can also cause less utility or energy consumption, resulting in additional cost savings. The controller 146 may also allow controlled variables to be controlled closer to their constraints, allowing the system 100 to operate in an improved or optimum manner. In addition, use of the controller 146 could result in less equipment maintenance and its associated costs.

Figure 2:
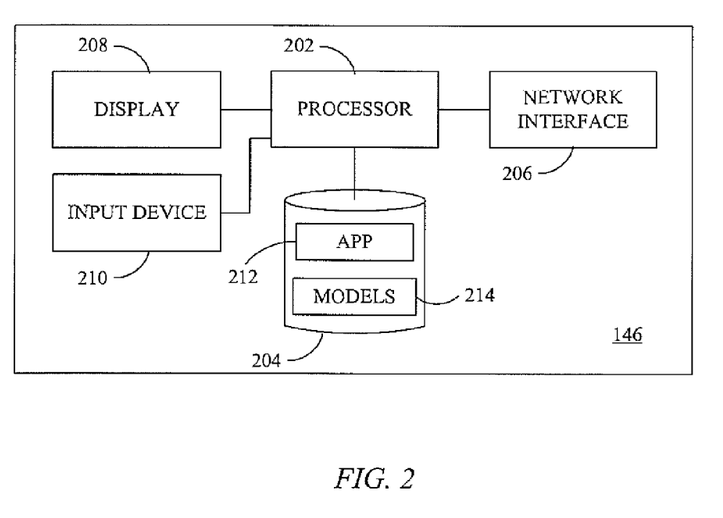
FIG. 2 illustrates an example multivariable controller for optimizing operation of the system of FIG. 1 according to this disclosure.

The controller 146 includes any suitable structure for controlling one or more systems 100, such as a controller implemented using hardware or a combination of hardware and software/firmware instructions. An example embodiment of the multivariable controller 146 is shown in FIG. 2, which is described below. As a particular example, the multivariable controller 146 could represent a controller implemented using PROFIT CONTROLLER from HONEYWELL INTERNATIONAL INC. (previously known as Robust Multivariable Predictive Control Technology or "RMPCT"). In other embodiments, the multivariable controller 146 could include an EXPERION OPC server, an EXPERION HS server, an EXPERION server pair, or an EXPERION EAS server from HONEYWELL INTERNATIONAL INC.

Depending on the implementation, the multivariable controller 146 could be configured to directly control components in the system 100. The multivariable controller 146 could also be configured to control the components in the systems 100 indirectly, such as through one or more other intermediary controllers. In those configurations, the other controllers could receive data from the multivariable controller 146 defining how the system 100 should be controlled and then implement that control. The other controllers could include any suitable structure(s) for controlling the system 100 or portions thereof. One example type of controller that could be utilized is an HC900 controller from HONEYWELL INTERNATIONAL INC.

The network 130 facilitates communication between various components in the system 100. For example, the network 130 could transport measurement data from the sensors 121-128 and weather station 129 to the multivariable controller 146 and provide control signals from the multivariable controller 146 to the various actuators. The network 130 may represent any suitable network or combination of networks. As particular examples, the network 130 could represent an Ethernet network, an electrical signal network (such as a HART or FOUNDATION FIELDBUS network), a pneumatic control signal network, or any other or additional type(s) of network(s).

Although FIG. 1 illustrates one example of a system 100 for controlling a mixture of fluid and an autotrophic organism, various changes may be made to FIG. 1. For example, the functional division in FIG. 1 is for illustration only. Various components in FIG. 1 could be omitted, combined, or further subdivided and additional components could be added according to particular needs. Additionally, the functionality of the controller 146 could be used in any other suitable system.

FIG. 2 illustrates an example multivariable controller 146 for optimizing operation of the system 100 of FIG. 1 according to this disclosure. The embodiment of the multivariable controller 146 shown in FIG. 2 is for illustration only. Other embodiments of the multivariable controller 146 could be used without departing from the scope of this disclosure. Also, while the multivariable controller 146 is described as being used in the system 100 of FIG. 1, the multivariable controller 146 could be used in any other suitable system. In addition, as noted above, any other suitable controller could be used to control autotroph cultivation.

In this example, the multivariable controller 146 includes at least one processor 202, at least one memory 204, at least one network interface 206, a display 208, and at least one input device 210. The processor 202 represents any suitable processing device, such as a microprocessor, microcontroller, digital signal processor, application-specific integrated circuit, field programmable gate array, or other logic device. The memory 204 represents any suitable volatile and/or non-volatile storage and retrieval device or devices, such as random access or read-only memory. The network interface 206 represents any suitable interface for facilitating communication over a network, such as an Ethernet interface or other electrical signal line interface or a wireless interface. The network interface 206 could, for example, receive measurement data identifying current values of controlled variables and output control signals for adjusting manipulated variables. The display 208 represents any suitable display for presenting information to a user. The input device 210 represents any suitable device or devices for receiving input from a user, such as a keyboard or mouse.

As shown in FIG. 2, the memory 204 includes one or more software applications 212 and one or more models 214. The software applications 212 represent one or more computer programs defining how the multivariable controller 146 controls one or more systems 100. For example, the software application 212 could use the models 214 to analyze input data (such as measurements of different controlled variables) to generate output signals (such as control signals for adjusting manipulated variables).

The one or more models 214 define relationships between the manipulated and disturbance variables and the controlled variables. The models 214 are used by the multivariable controller 146 to control the one or more controlled variables in one or more algae tanks 104. Each algae tank 104 could have its own set of models, or multiple algae tanks 104 could have at least one common model. In some embodiments, each model 214 could associate a single manipulated or disturbance variable to a single controlled variable.

In particular embodiments, a model 214 may be adapted over time to account for the actual interaction of components and how they affect various characteristics measured by the sensors 121-128 and the weather station 129. Thus, the models 214 can be changed over time based on the actual measured responses detected by the sensors to changes in the manipulated variables.

As part of the control of the systems 100, the multivariable controller 146 could use the models 214 to make adjustments to manipulated variables so that controlled variables are maintained within specified limits. Also, the multivariable controller 146 could do this while helping to ensure that certain process objectives are met. For example, the process objectives could include maintaining a healthy algae level as represented by, for example, pH and/or dissolved carbon dioxide level. The process objectives could also include controlling the algae tank 104 so that more expensive component manipulations are minimized.

Using these models 214, the multivariable controller 146 can effectively control the controlled variables through adjustments to the manipulated variables and/or consideration of the disturbance variables. The multivariable controller 146 can optimize the operation of the system 100 using these models 214 and one or more economic optimization approaches. In some embodiments, the multivariable controller 146 is configured to use either linear program (LP) economics or quadratic program (QP) economics when controlling the system 100. These two economic optimization approaches use a simple minimization strategy, although the quadratic optimization also uses ideal resting values (or desired steady state values). The economics can be defined to meet various objectives. These objectives could include minimizing overall energy or chemical usage in the system 100.

In particular embodiments, an algal biomass growth (X) during its exponential phase could be represented as:

$$X(t)=X_0 e^{\mu \cdot t}.$$

A model for the specific growth rate ($\mu$) may be represented as:

$$\mu_g(t)=\mu(S) \cdot \mu(X) \cdot \mu(pH) \cdot \mu(T) \cdot \mu(I) \ldots.$$

where $\mu(S)$ represents the effect of dissolved carbon dioxide, $\mu(X)$ represents the effect of biomass concentration, $\mu(pH)$ represents the effect of pH, $\mu(T)$ represents the effect of temperature, and $\mu(I)$ represents the effect of light intensity. Other components may be considered in the model as indicated by the ellipses ( . . . ) in the above equation.

As seen here, an optimization of this model may involve a large number of process variables, each able to be incorporated into either a linear or quadratic optimization objective. The multivariable controller 146 can optimize the controlled variables using this optimization to meet various ones of the objectives described above.

In some embodiments, the models 214 could be generated for the system 100 based on step-testing of the various components in the system 100. Additionally, in some situations, these variables may be "out of phase" with one another, such as when a change to one manipulated variable has an immediate effect on a first controlled variable and a delayed effect on a second controlled variable. To improve the models 214, a lag can be added to one or more of the measurement data from the sensors 121-128 or weather station 129, bringing the measurement data into phase and resulting in more accurate models. The amount of lag can be determined by examining the measurement data for a particular implementation of the system 100.

In particular embodiments, the models 214 may be used to optimize a goal function, such as lipid production, biomass growth rate, or nutrient removal. In order to optimize the goal function, there may be an optimization of manipulated variables to drive the controlled variables to at least one target for the controlled variables. Additionally, a value may be calculated for the at least one target that optimizes the goal function.

Although FIG. 2 illustrates one example of a multivariable controller 146 for optimizing operation of the system 100 of FIG. 1, various changes may be made to FIG. 2. For example, the controller 146 could include any other or additional components according to particular needs. Also, while shown as being formed using a processing device, the controller 146 could be implemented in any other suitable manner. As a particular example, the functions described above as being performed by the controller 146 could be implemented using any other control technology. Further, the controller 146 could be used to control one or multiple algae tanks 104 or systems 100. In addition, the details provided above (such as the identification of particular controlled, manipulated, and disturbance variables and models 214) are examples only. The controller 146 could operate using any other suitable variables and/or models.

Figure 3:
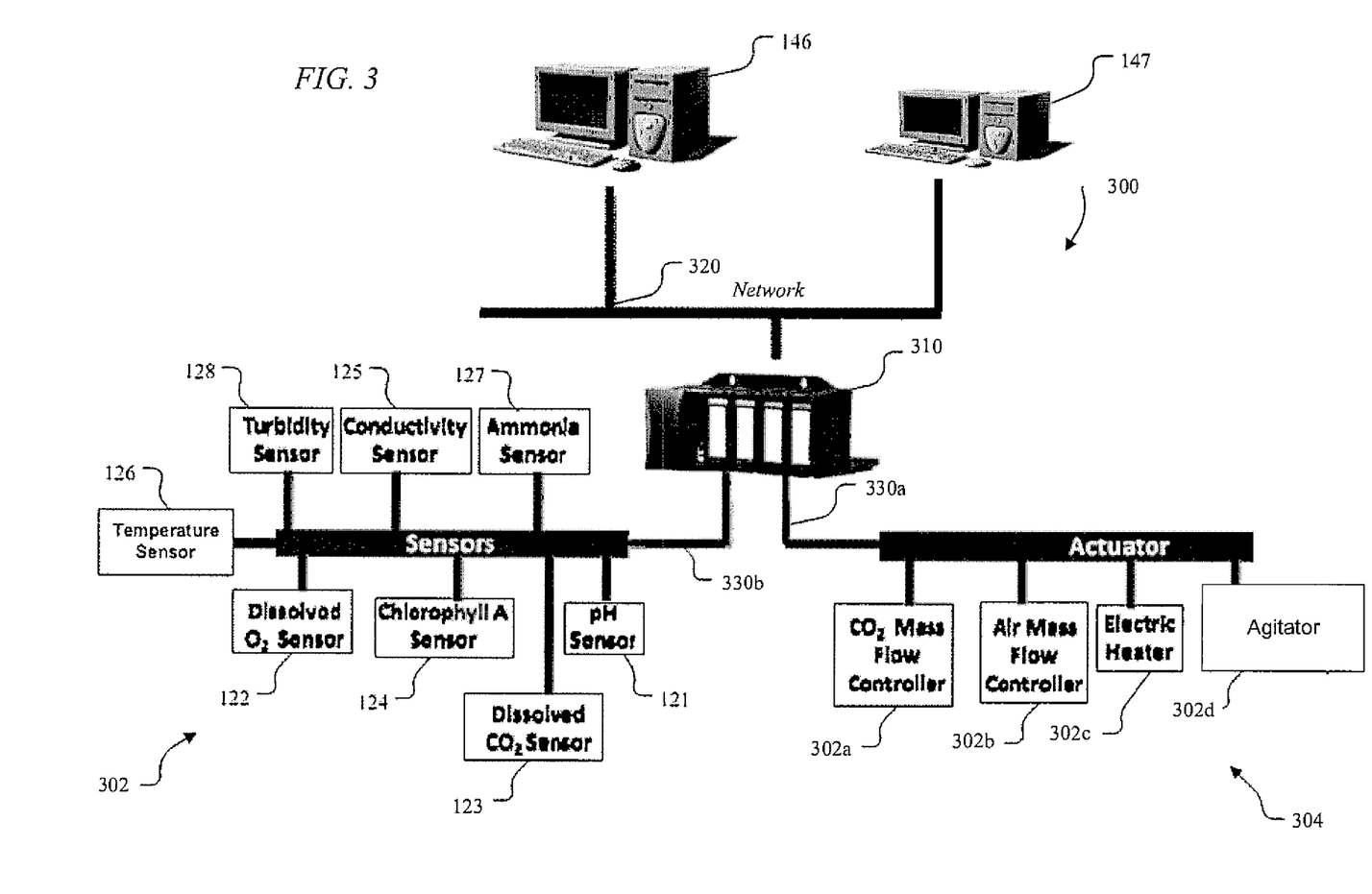
FIG. 3 illustrates an example networked system for controlling a mixture of fluid and an autotrophic organism according to this disclosure.

FIG. 3 illustrates an example networked system 300 for controlling a mixture of fluid and an autotrophic organism according to this disclosure. As described below, certain elements in FIG. 3 may correspond to elements in FIGS. 1 and 2 described above. As a result, reference numerals from FIGS. 1 and 2 are repeated in FIG. 3 where appropriate.

In this example, the system 300 includes sensors 302, actuators 304, a multivariable controller 146, a server 147, a local controller 310, and networks 320, 330a, and 330b. The networks 320, 330a, and 330b may include any suitable communication networks. The sensors 302 provide multiple inputs to the multivariable controller 146. For example, information may be communicated from the sensors 302 through the network 330b, the controller 310 and the network 320 to the multivariable controller 146. The sensors 302 may correspond to the same sensors 121-128 in FIG. 1. Although not shown, the weather station 129 could also provide data to the controller 146.

The actuators 304 may correspond to multiple outputs from the multivariable controller 146. For example, commands may be communicated from the controller 146 through the network 320, the controller 310, and the network 330a to the actuators 304. A carbon dioxide mass flow rate controller 302a could include the valve 114b of FIG. 1. An air mass flow rate controller 302b could include the valve 112b of FIG. 1. An electric heater 302c could correspond to the thermal energy component 115 and electrical immersion heater 115b of FIG. 1. An agitator 302d may include the mixing component 119 of FIG. 1. Although not shown, other actuators shown in FIG. 1 may also be included in FIG. 3.

As described above, in particular configurations, the multivariable controller 146 can utilize an intermediary for communications. As shown in FIG. 3, the intermediary is the local controller 310, which relays information from the sensors 302 to the controller 146 and commands from controller 146 to the actuators 304. In certain configurations, the controller 310 may be an HC900 controller by HONEYWELL INTERNA- TIONAL INC. Also, the server 147 may be used to store and visualize process data. As one example, the server 147 may be a HONEYWELL EXPERION HS. In particular embodiments, more than one server 147 may be supplied.

Although FIG. 3 illustrates one example of a networked system 300 for controlling a mixture of fluid and an autotrophic organism, various changes may be made to FIG. 3. For example, the multivariable controller 146 could be used in any other suitable system. Additionally, as described above, other types of controller(s) may be used instead of a multivariable controller, such as PID controllers, model predictive controllers, and the like.

Figure 4:
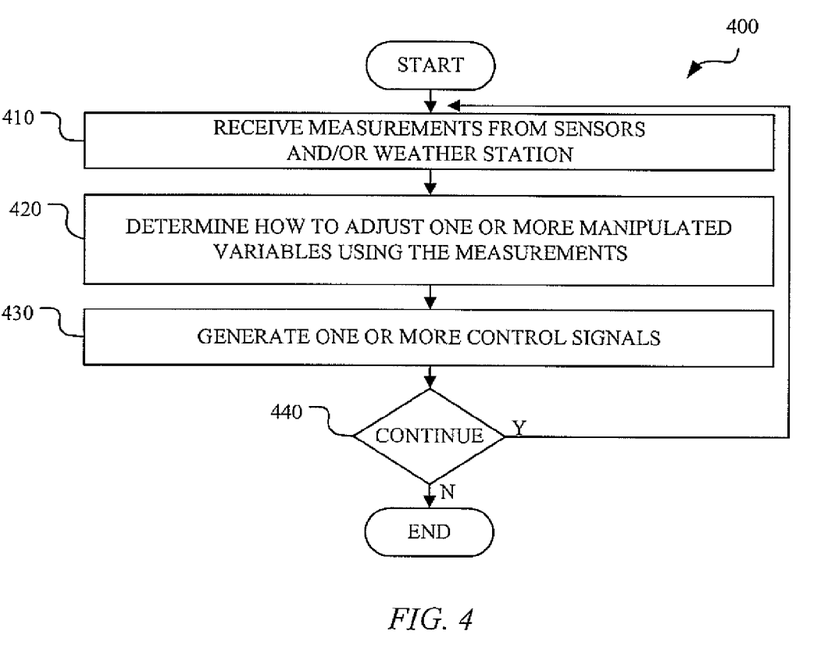
FIG. 4 illustrates an example process for controlling a system with a mixture of fluid and an autotrophic organism according to this disclosure.

FIG. 4 illustrates an example process 400 for controlling a system with a mixture of fluid and an autotrophic organism according to this disclosure. At step 410, measurements are received from sensors and/or a weather station. The sensors may be the sensors 121-128 in FIG. 1, although other or additional sensors could be used. In particular configurations, a sensor may correspond to a controlled variable. As described in FIG. 1, the information from the weather station 129 may include measurements of an ambient environment. The measurements may be received by the multivariable controller 146 or other controller.

At step 420, one or more adjustments to one or more manipulated variables are determined using the measurements. This could include using one or more models 214 that are associated with any suitable manipulated, controlled, and disturbance variables.

At step 430, one or more control signals are generated based on the determined adjustment(s). These control signals may actuate one or more of the actuators described above. As particular examples, the control signals could cause adjustments to the carbon dioxide flow rate, air flow rate, water temperature, or agitation level in the tank 104.

At decisional step 440, a determination may be made as to whether to continue. If so, the process 400 returns to step 410. This could be done, for example, at a specified interval, like once every thirty seconds.

Although FIG. 4 illustrates one example of a process 400 for controlling a system with a mixture of fluid and an autotrophic organism, various changes may be made to FIG. 4. For example, while shown as a series of steps, various steps in FIG. 4 could overlap, occur in parallel, occur in a different order, or occur any number of times.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The term "couple" and its derivatives refer to any direct or indirect communication between two or more elements, whether or not those elements are in physical contact with one another. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system, or part thereof that controls at least one operation. A controller represents any suitable structure, such as hardware or a combination of hardware and software/firmware instructions. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
a controller configured to receive measurements from multiple sensors, apply at least one lag to the measurements from at least one of the sensors, and determine how to adjust one or more manipulated variables to control multiple controlled variables using the measurements, the one or more manipulated variables and the controlled variables associated with a mixture of fluid containing at least an autotrophic organism;
wherein the controlled variables include a dissolved carbon dioxide concentration of the mixture;
wherein the one or more manipulated variables include a carbon dioxide flow rate for the mixture; and
wherein the at least one lag is defined based on different response times of two or more controlled variables to a change in the one or more manipulated variables.

2. The apparatus of claim 1, wherein the controlled variables further include a pH level of the mixture.

3. The apparatus of claim 1, wherein the one or more manipulated variables further include at least one of: an air flow rate, a water temperature, a macronutrients dosing, a micronutrients dosing, and an agitation level for the mixture.

4. The apparatus of claim 1, wherein the controller is further configured to provide one or more control signals to one or more actuators associated with the one or more manipulated variables.

5. The apparatus of claim 1, wherein:
the controller is further configured to determine how to adjust the one or more manipulated variables based in part on one or more disturbance variables; and
the one or more disturbance variables include at least one of: an ambient light intensity, an ambient temperature, a fluid composition, algae speciation, a wind condition, a presence of one or more predators, and a presence of bacteria.

6. The apparatus of claim 1, wherein the autotrophic organism is algae.

7. The apparatus of claim 1, wherein:
the controller is configured to use at least one model that relates the dissolved carbon dioxide concentration to the one or more manipulated variables;

the controller is configured to use the at least one model to adjust the one or more manipulated variables to drive the dissolved carbon dioxide concentration to at least one target that optimizes a goal function; and the goal function is to optimize at least one of: biomass growth rate, nutrient removal, and lipid production.

8. The apparatus of claim 7, wherein the controller is configured to optimize the goal function by:

optimizing the one or more manipulated variables to drive the controlled variables to at least one target; and calculating a value for the at least one target that optimizes the goal function.

9. The apparatus of claim 1, wherein the controller is configured to determine how to adjust the one or more manipulated variables using one of: a linear program optimization and a quadratic program optimization.

10. The apparatus of claim 1, wherein the controller is further configured to update a model based on measured changes to the controlled variables upon adjustment to the one or more manipulated variables.

11. A method comprising:

receiving, at a controller, measurements from multiple sensors including measurements of a dissolved carbon dioxide concentration of a mixture of fluid containing at least an autotrophic organism;

applying at least one lag to the measurements from at least one of the sensors;

determining an adjustment to one or more manipulated variables to control multiple controlled variables using the measurements; and generating one or more signals to modify the one or more manipulated variables based on the determined adjustment;

wherein the controlled variables include the dissolved carbon dioxide concentration of the mixture;

wherein the one or more manipulated variables include a carbon dioxide flow rate for the mixture; and wherein the at least one lag is defined based on different response times of two or more controlled variables to a change in the one or more manipulated variables.

12. The method of claim 11, wherein the measurements further include measurements of a pH level of the mixture.

13. The method of claim 11, wherein the one or more manipulated variables further include at least one of: an air flow rate, a water temperature, and an agitation level for the mixture.

14. The method of claim 11, wherein:

at least one model relates the dissolved carbon dioxide concentration to the one or more manipulated variables;

determining the adjustment includes using the at least one model to adjust the one or more manipulated variables to drive the dissolved carbon dioxide concentration to at least one target that optimizes a goal function; and the goal function is to optimize at least one of: biomass growth rate, nutrient removal, and lipid production.

15. The method of claim 11, wherein the mixture of fluid includes at least one of: fresh water, salt water and wastewater.

16. The method of claim 11, wherein:

the adjustment to the one or more manipulated variables is based in part on one or more disturbance variables; and the one or more disturbance variables include at least one of: an ambient light intensity, an ambient temperature, a fluid composition, algae speciation, a wind condition, a presence of one or more predators, and a presence of bacteria.

17. The method of claim 11, wherein the autotrophic organism is algae.

18. The method of claim 11, wherein determining the adjustment comprises determining how to adjust the one or more manipulated variables using one of: a linear program optimization and a quadratic program optimization.

19. A non-transitory computer readable medium embodying a computer program, the computer program comprising:

computer readable program code for receiving, at a controller, measurements from multiple sensors including measurements of a dissolved carbon dioxide concentration of a mixture of fluid containing at least an autotrophic organism;

computer readable program code for applying at least one lag to the measurements from at least one of the sensors;

computer readable program code for determining an adjustment to one or more manipulated variables to control multiple controlled variables using the measurements; and computer readable program code for generating one or more control signals to modify the one or more manipulated variables based on the determined adjustment;

wherein the controlled variables include the dissolved carbon dioxide concentration of the mixture;

wherein the one or more manipulated variables include a carbon dioxide flow rate for the mixture; and wherein the at least one lag is defined based on different response times of two or more controlled variables to a change in the one or more manipulated variables.

20. The computer readable medium of claim 19, wherein the measurements further include measurements of a pH level of the mixture.

21. The computer readable medium of claim 19, wherein the one or more manipulated variables further include at least one of: an air flow rate, a temperature, and an agitation level for the mixture.

22. The computer readable medium of claim 19, wherein:

at least one model relates the dissolved carbon dioxide concentration to the one or more manipulated variables;

the computer readable program code for determining the adjustment includes computer readable program code for using the at least one model to determine how to adjust the one or more manipulated variables to drive the dissolved carbon dioxide concentration to at least one target that optimizes a goal function; and the goal function is to optimize at least one of: biomass growth rate, nutrient removal, and lipid production.

23. The apparatus of claim 1, wherein the controller is configured to receive measurements from a pH sensor, a dissolved oxygen sensor, a dissolved carbon dioxide sensor, a chlorophyll sensor, a conductivity sensor, a temperature sensor, a macronutrients sensor, and a turbidity sensor.

* * * * *